United States Patent [19]
Garlich et al.

[11] Patent Number: 5,320,829
[45] Date of Patent: Jun. 14, 1994

[54] ORAL COMPOSITIONS FOR INHIBITING PLAQUE FORMATION

[75] Inventors: Joseph R. Garlich; R. Keith Frank, both of Lake Jackson; Jaime Simon, Angleton; Garry E. Kiefer, Lake Jackson; David A. Wilson, Richwood, all of Tex.

[73] Assignee: The Dow Chemical Company, Midland, Mich.

[21] Appl. No.: 805,598

[22] Filed: Dec. 10, 1991

[51] Int. Cl.$^5$ ............................ A61K 7/16; A61K 7/22
[52] U.S. Cl. ................................. 424/54; 424/49; 424/57
[58] Field of Search .................................. 424/49–58

[56] References Cited

U.S. PATENT DOCUMENTS

| | | |
|---|---|---|
| Re. 29,182 | 4/1977 | McCune et al. |
| 3,488,419 | 1/1970 | McCune et al. |
| 3,860,576 | 1/1975 | Ham et al. |
| 3,925,456 | 12/1975 | Ploger et al. ............ 424/54 |
| 3,941,772 | 3/1976 | Ploger et al. ............ 424/54 |
| 3,984,543 | 10/1976 | Ploger et al. ............ 424/54 |
| 3,988,443 | 10/1976 | Ploger et al. ............ 424/49 |
| 4,001,212 | 1/1977 | Richman |
| 4,064,164 | 12/1977 | Blum et al. |
| 4,098,880 | 7/1978 | Gaffar |
| 4,100,270 | 7/1978 | Gaffar |
| 4,108,961 | 8/1978 | Ploger et al ............ 424/57 |
| 4,118,474 | 10/1978 | Gaffar et al. |
| 4,123,512 | 10/1978 | Gaffar |
| 4,137,303 | 1/1979 | Gaffar et al. |
| 4,161,518 | 7/1979 | Wen et al. |
| 4,168,265 | 9/1979 | Tabushi et al. |
| 4,174,428 | 11/1979 | Tabushi et al. |
| 4,177,258 | 12/1979 | Gaffar et al. |
| 4,183,915 | 1/1980 | Gaffar et al. |
| 4,215,105 | 7/1980 | Gaffar et al. |
| 4,224,308 | 9/1980 | Gaffar et al. |
| 4,224,309 | 9/1980 | Gaffar et al. |
| 4,243,658 | 1/1981 | Chang |
| 4,273,579 | 6/1981 | Gaffar et al. |
| 4,348,381 | 9/1982 | Gaffar et al. |
| 4,428,930 | 1/1984 | Chang |
| 4,459,241 | 7/1984 | Wilson et al. |
| 4,470,964 | 9/1984 | Chang |
| 4,485,090 | 11/1984 | Chang |
| 4,493,771 | 1/1985 | Wilson et al. |
| 4,540,508 | 9/1985 | Wilson et al. |
| 4,568,467 | 2/1986 | Crump et al. |
| 4,575,456 | 3/1986 | Hayes |
| 4,627,977 | 12/1986 | Gaffar et al. |
| 4,663,154 | 5/1987 | Ryan |
| 4,680,396 | 7/1987 | Crump et al. |
| 4,749,561 | 7/1988 | Lane et al. |
| 4,770,791 | 9/1988 | Crump et al. |
| 4,799,995 | 1/1989 | Crump et al. |
| 4,808,401 | 2/1989 | Gaffar et al. |
| 4,816,245 | 3/1989 | Gaffar |
| 4,820,507 | 4/1989 | Klueppel et al. |
| 4,882,142 | 11/1989 | Simon et al. |
| 4,915,937 | 4/1990 | Amjad |
| 4,937,333 | 6/1990 | Garlich et al. |
| 5,064,633 | 11/1991 | Simon et al. |
| 5,096,699 | 3/1992 | Gaffar et al. ............ 424/54 |

FOREIGN PATENT DOCUMENTS

| | | |
|---|---|---|
| 0208009A1 | 1/1987 | European Pat. Off. |
| 0363748A2 | 4/1990 | European Pat. Off. |
| 374501 | 6/1990 | European Pat. Off. |
| 375376 | 6/1990 | European Pat. Off. |
| 462787 | 12/1991 | European Pat. Off. |
| 92/00721 | 1/1992 | PCT Int'l Appl. |
| 2210264A | 6/1989 | United Kingdom |
| 2210265A | 6/1989 | United Kingdom |

OTHER PUBLICATIONS

Sherry et al. CA. 109: 69881z (1988).
Delgado et al., CA. 113: 240408(1990).
Wang et al. CA 113: 14960B(1990).
Garlich et al. CA 113: 172351(h)(1990) of U.S. 4937333.

*Primary Examiner*—Shep K. Rose

[57] ABSTRACT

Oral compositions and methods effective in promoting oral hygiene containing in an effective amount at least one cyclic alkylamine or cyclic amine as an antiplaque and/or antigingivitis agent.

8 Claims, No Drawings

ORAL COMPOSITIONS FOR INHIBITING PLAQUE FORMATION

BACKGROUND OF THE INVENTION

The present invention relates to oral compositions containing an antiplaque agent.

"Oral composition" means a composition for topical applications to the oral cavity to clean and care for the teeth as well as the oral cavity surfaces. Representatives of such compositions are oral hygiene products and dentifrices such as mouthwashes or rinses, toothpaste, dental gels, tooth powder, chewing gum, lozenges and similar products. In addition to cleaning teeth to remove dental plaque, the function of oral hygiene preparations is to stop the formation of dental calculus, to prevent dental disorders such as caries, periodontosis and gingivitis, and also to eliminate halitosis.

Dental calculus, or tartar as it is sometimes called, is a hard mineralized material which forms on teeth that consists of inorganic and organic components. The inorganic portion is largely calcium and orthophosphate arranged in a crystal lattice called hydroxyapatite (HAP). The organic portion is derived mainly from microorganisms (i.e., bacteria, yeast, etc.) as well as epithelial cells, white blood cells and food debris.

Formation of dental calculus occurs in two steps. In the first step, plaque is deposited on the teeth. "Plaque" is a deposit which forms on teeth and consists of inorganic and organic components derived from saliva, food and bacteria which are present in the oral cavity. Most of the plaque consists of dead and living bacteria surrounded by a gel-like matrix derived from the bacteria and saliva. In the second phase, plaque undergoes calcification to form dental calculus. Initially, amorphous deposits of calcium phosphate begins to appear on and within the matrix of the dental plaque. As the aggregates of calcium phosphate become sufficiently closely packed together, they crystallize to form HAP. The amorphous calcium phosphate, although related to hydroxyapatite, differs from it in crystal structure, particle morphology and stoichiometry.

The presence of both the bacteria and the plaque deposits is detrimental to the health of the teeth and gums. If the bacteria and the plaque formation are not checked, they may result in infected gingival tissue, the formation of dental caries and periodontal disease.

A wide variety of chemical and biological agents have been suggested in the art to retard calculus formation or to remove calculus after it is formed. Mechanical removal of this material periodically by the dentist is, of course, routine dental office procedure.

In addition to being an integral step for the formation of calculus, consequences of the presence of plaque include gingivitis, periodontitis, tooth decay (dental caries) and denture associated problems. Inhibition of oral bacteria involved in the formation of plaque by antibiotics or antiseptic agents is one means to retard the formation of plaque, thus aiding in preventing or controlling the formation of dental calculus and other plaque related diseases. ; see, for example, P.S. Hull, *J. Clinical Periodontology* 7, 431-442 (1980). Examples of antiseptic agents include amidines, such as chlorhexidine and alexidine, and numerous antibacterially active quaternary ammonium compounds, such as cetylpyridinium chloride or the quaternary ammonium compounds described in U.S. Pat. No. 3,369,046; U.S. Pat. No. 4,820,507; and quaternary ammonium organosiloxane compounds described in U.S. Pat. No. 4,161,518.

Although the quaternary ammonium compounds are rapidly adsorbed onto the tooth surface, they exhibit only a moderate degree of efficacy as antiplaque agents as they are rapidly released from the tooth surface and thus retained in the oral cavity for only a short period of time. Chlorhexidine has been the most successful antiplaque agent and is retained in the oral cavity by binding to anionic groups mainly on the oral mucosa. The use of chlorhexidine in oral preparations however, suffers from the following disadvantages: (1) a prolonged bitter aftertaste lasting up to several hours; (2) after prolonged use they produce stains on the teeth, tongue, gums, oral mucosa and dental restorations; and (3) local irritation of the oral mucosa and tongue.

Another means to prevent plaque and calculus formation is to coat the teeth with a material to prevent the release of previously applied therapeutic agents or to coat the teeth with a material containing an antimicrobial agent. U.S. Pat. Nos. 4,243,658; 4,428,930; 4,470,964 and 4,485,090 disclose a dentifrice composition containing a water-dispersible, membrane-forming material which, when applied to tooth surfaces forms a hydrophobic barrier thereon which substantially reduces elution of a previously applied therapeutic agent. A varnish containing an antimicrobial agent, which provides the sustained release of the antimicrobial agent over a period of at least four days was disclosed in U.S. Pat. No. 4,496,322. The use of the therapeutic agent or varnish coating are not entirely satisfactory as their application requires a qualified professional, making their use as part of routine oral hygiene maintenance impractical.

As the formation of calculus requires the crystallization of HAP, agents which effectively interfere with crystal growth, including HAP, can be effective as antiplaqueanticalculus agents. Inhibition of crystalline HAP formation can therefore be achieved by compounds which chelate calcium ions, which prevents the calculus from forming and/or breaks down mature calculus by removing calcium. It is known in the prior art that water soluble hexametaphosphates, tripolyphosphates and pyrophosphates and the like, are effective calcium and magnesium ion threshold agents, sequestrants and/or chelating agents. A threshold agent has the ability to prevent the precipitation of certain scale forming salts (e.g., calcium carbonate) at concentrations that are much lower than the amount needed for sequestration. See, for example, U.S. Pat. No. 3,488,419 which discloses oral compositions containing polyphosphonate and U.S. Pat. No. 4,215,105 which discloses oral compositions containing phosphonoacetic acid. The effectiveness of polyphosphonates as antiplaque agents has been limited as they are significantly hydrolyzed by salivary enzymes (phosphatases) to orthophosphates which are ineffective as inhibitors of HAP formation. The amount of enzymatic hydrolysis of the polyphosphate has been reduced by the use of a linear molecularly dehydrated polyphosphate salt combined with fluoride as described in U.S. Patent No. 4,808,410.

It would therefore be desirable to have an oral composition containing an effective antiplaque agent to aid in the prevention of caries and gingivits which does not stain the teeth and is not subject to inactivation by enzymatic hydrolysis. It would also be desirable to provide an improved means whereby antimicrobial compound can be retained within the oral cavity for a longer period of time.

SUMMARY OF THE INVENTION

The present invention relates to an oral composition containing an antiplaque agent. In particular, the present invention relates to oral an composition comprising an orally acceptable vehicle containing therein an effective amount as an antiplaque agent a cyclic alkylamine or a cyclic amine selected from one or more of the compounds represented by the formulae I to IV:

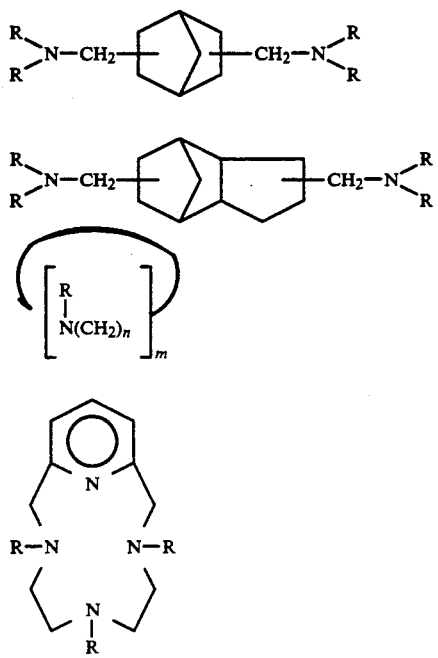

wherein each R is independently selected from hydroen, hydrocarbon radical haivng from 1-8 carbon atoms, hydroxyalkyl (wherein the alkyl group contains 2-6 carbon atoms), and

wherein

Z is independently —PO$_3$H$_2$, —COOH, —H, C$_1$-C$_{18}$ alkyl or a physiologically acceptable salt of the acid radicals; and X and Y are independently —H, or hydrocarbon radicals having from 1 to 3 carbon atoms; with the proviso that each cyclic alkylamine or cyclic amine has at least two Z groups which are —PO$_3$H$_2$, or a physiologically acceptable salt thereof;

each n within the ring is independently 2 or 3; and m is 3 to 6, inclusive;

n and m being selected such that the total number of carbon and nitrogen atoms in the cyclic amine ring does not exceed 18.

As used herein, the term "alkyl" means a linear or branched alkyl; and thus, secondary and tertiary amines are included. The alkyl terms up to C$_{20}$ included, for example, t-butyl, sec-butyl, isobutyl, and in like manner all such branched or straight chain alkyls.

In another embodiment of the present invention there is provided an oral composition containing a cyclic amine and an antimicrobial quaternary ammonium compound. The combination provides that the antimicrobial quaternary ammonium compound is retained within the oral cavity, especially on the tooth surface, for a longer period of time. The enhanced retention of the antimicrobial quaternary ammonium compound within the oral cavity increases the time period during which the compound will be effective as an antiplaque agent and/or antigingivitis agent.

A further embodiment of the present invention takes the form of an oral composition containing a cyclic amine, antimicrobial quaternary ammonium compound and a metal ion for enhanced retention of the quaternary ammonium compound within the oral cavity.

In yet another embodiment of the present invention, there is provided an improved method of inhibiting the formation of dental plaque and gingivitis.

The present invention also provides an improved method for the reduction of undesirable dental plaque and/or gingivitis.

DETAILED DESCRIPTION OF THE INVENTION

This invention relates to an oral composition containing in an orally acceptable vehicle an effective amount of an antiplaque and/or antigingivitis cyclic alkylamine or cyclic amine. An "orally acceptable vehicle" means a medium in which an antiplaque agent may be administered to the oral cavity without substantial harmful effects to the oral cavity surfaces. An "effective amount" is that which will inhibit or reduce the formation of plaque and/or gingivitis in the oral cavity.

As bacterial plaque is a main etiological factor in gingivitis, periodontitis, tooth decay (dental caries) and other dental associated problems, the ability to control dental plaque aids in preventing and/or controlling gingivitis, periodontitis and dental caries. Thus as used herein, "antiplaque" means antiplaque and/or antigingivitis and/or antiperiodontitis and/or anticaries. In addition, as the volatile sulfur compounds associated with oral malodor are related to the gingival health, as well as being produced by the putrefactive activity of microorganisms, as used herein, an antiplaque agent will also aid in the control of oral malodor.

Cyclic alkylamines of the present invention are derivatives of bicycloheptadiene as given in formula (I)

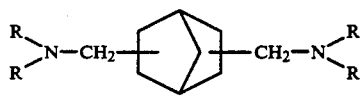

or derivatives of dicyclopentadiene as given in formula (II)

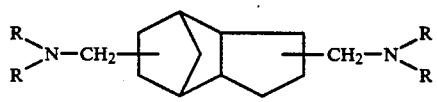

wherein each R is independently —H, hydrocarbon radical having from 1-8 carbon atoms; hydroxyalkyl (wherein the alkyl group contains 2-6 carbon atoms), or

wherein

Z is independently —PO$_3$H$_2$, —COOH, —H, C$_1$-C$_{18}$ alkyl or a physiologically acceptable salt of the acid radicals; and X and Y are independently —H, or hydrocarbon radicals having from 1 to 3 carbon atoms;

with the proviso that each cyclic alkylamine has two Z groups which are —PO$_3$H$_2$, or a physiologically acceptable salt thereof. A physiologically acceptable salt refers to the acid addition salts, or mixtures thereof, of those bases which will form a salt which does not cause a significant adverse physiological effect when used in an oral product consistent with good pharmacological practice. Examples of suitable salts include those of the alkali metal, alkaline-earth metal and mixtures thereof.

Methods for preparing compounds of Formulae I-III are known in the art and reference made thereto for the purpose of this invention. For example, the cyclic alkylamines of Formulae I and II can be prepared from commercially available dicyclopentadiene (DCPD) and bicycloheptadiene (BCHD). Electrophilic addition reactions are known to form the nitrile or dinitrile by reacting the double bonds of DCPD or BCHD with hydrogencyanide (HCN). The nitrile can then be hydrolyzed to form the carboxylic acid derivative. The DCPD or BCHD can also be reacted with HCN followed by reduction to obtain the bis methylamine derivative; this product in turn can be reacted with glycolonitrile in the presence of caustic to give the sodium salt of tetraacetic acid of the bisamine.

Cyclic amines of the present invention are macrocyclic amines of Formula (III):

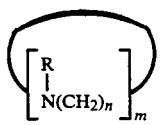
(III)

or Formula (IV):

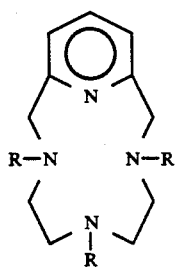
(IV)

wherein each n is independently 2 or 3 and m is 3 to 6, inclusive, n and m being selected such that the total number of carbon and nitrogen atoms in the cyclic amine ring does not exceed 18; and each R is as defined hereinbefore.

Polyazamacrocycles useful as starting materials which can be derivatized to form the cyclic aminophosphonates of formula III of the present invention include 1,4,7-triazacyclononane, 1,4,7,10-tetraazacyclododecane, 1,4,8,11-tetraazacyclotetradecane, 1,4,7,10,13-pentaazacyclopentadecane, 1,4,7,10,13,16-hexaazacyclooctadecane, and the like. These polyazamacrocycles may be prepared by documented methods such as T.J. Atkins et al., *J. Amer. Chem. Soc.*, 96, 2268-70 (1974) and T.J. Richman et al., *Org. Synthesis*, 58, 86-98 (1978). The preferred starting material, 1,4,7,10-tetraazacyclododecane, for polyazamacrocycles of formula III is commercially available. Derivatization of the polyazamacrocycles means the reaction of the amine with the appropriate reactive compound to give an R group as defined hereinbefore.

Polyazamacrocycles useful as starting materials for the cyclic aminophosphonates of Formula IV of the present invention are prepared by the procedures set forth in U.S. patent application Ser. No. 07/805,551 filed Dec. 10, 1991, filed on even date herewith and entitled "Bicyclopolyazamacrocyclophosphonic Acids, and Complexes and Conjugates Thereof for Use as Contrast Agents", by Garry Kiefer, Jamie Simon and Joseph R. Garlich, the disclosure of which is hereby incorporated by reference. In general, compounds of Formula IV are synthesized by the following reaction scheme.

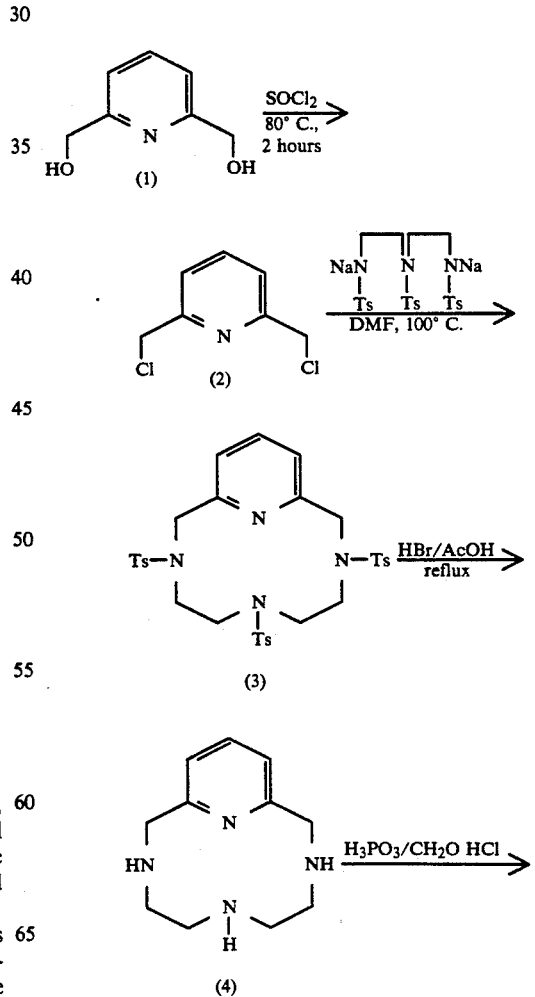

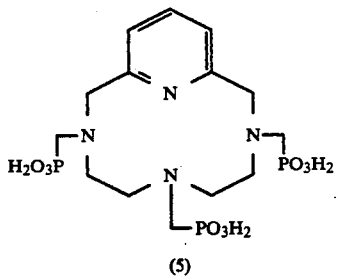

(5)

Aminophosphonio acids can be prepared by a number of known synthetic techniques. Of particular importance is the reaction of a compound containing at least one reactive amine hydrogen with a carbonyl compound (aidehyde or ketone) and phosphorous acid or derivative thereof as described in U.S. Pat. No. 3,288,846, the disclosure of which is hereby incorporated by reference, and described by Moedritzer and Irani, *J. Org. Chem.*, 31, 1603 (1966). For example, p-nitrobenzyl ethylenediamine reacted with formaldehyde and phosphorous acid can be converted to the p-nitrobenzyl ethylenediaminetetramethylenephosphonic acid. Reduction of the nitro group would yield p-aminobenzyl ethylenediaminetetramethylenephosphonic acid. The preparation of cyclic aminophosphonates of Formula III of the present invention can also be found in U.S. patent application Ser. No. 07/284,876, the disclosure of which is hereby incorporated by reference. In a preferred embodiment of the present invention, all the R substituents of Formulae I-IV are methylene phosphonic acid.

Carboxymethylation of the amines of the present invention may be performed by the method of Desreux using bromoacetic acid derivatives and a suitable base [J.F. Desreux, *Inorg. Chem.* 19, 1319–24 (1980)].

Methods for carboxyalkylating to give amine derivatives containing a carboxyalkyl group are well known, see, for example, U.S. Pat. No. 3,726,912, the disclosure of which is hereby incorporated by reference, as are the methods which give alkyl phosphonio and hydroxyalkyl substituents on the amine nitrogens, see, for example U.S. Pat. No. 3,398,198, the disclosure of which is hereby incorporated by reference.

The cyclic alkylamines or cyclic amines of the present invention are typically present in an oral composition in a concentration of from about 0.5 millimolar (mM) to about 20 mM, preferably in the range of about 1 mM to about 10 mM, and more preferably about 1 mM to about 2 mM.

In certain highly preferred forms of the invention, the oral compositions are substantially liquid in character, such as a mouthwash or rinse. In such a preparation the vehicle can be water or is a water-alcohol mixture, although alcohol is not required. When alcohol is present, the weight ratio of water to alcohol is in the range of from about 1:1 to about 20:1, preferably about 3:1 to 10:1 and more preferably about 4:1 to about 6:1. The total amount water or water-alcohol mixture in this type of preparation is typically in the range of from about 70 percent to about 99.92 percent by weight of the preparation.

The pH of such liquid and other preparations of the invention is generally in the range of from about 4.5 to about 9 and typically from about 5.5 to about 8. The pH is preferably in the range of from about 6 to about 8.

A variety of other ingredients may be added to the dentifrices of the present invention. Thus, for example, prophylactic agents, polishing agents, soaps or detergents, flavoring and sweetening agents, thickening agents and humectants may be included using techniques which are known to the art.

In certain other desirable forms of this invention, the oral composition may be substantially solid or semisolid in character, such as toothpowder, a dental tablet, a toothpaste, gel or dental cream. The vehicle of such solid or semisolid oral preparations generally contains added polishing material more fully described hereinafter.

Representative prophylactic agents include supplemental caries-preventing materials such as sodium fluoride, stannous fluoride, potassium fluoride, hexylamine hydrofluoride, myristylamine hdyrofluoride, betaine fluoride, glycine potassium fluoride, etc. A particularly preferred fluoride is sodium fluoride. Typically these prophylactic agents are present in sufficient concentrations so as to provide an available fluoride ion concentration of up to about 2 percent by weight, and preferably in the range of about 0.5-2 percent by weight, of the dentifrice composition.

Suitable polishing agents include, for example, abrasive materials such as insoluble condensed phosphates such as calcium pyrophosphate, insoluble calcium polyphosphate (also known as calcium polymetaphosphate) and highly polymerized sodium polyphosphate; and water impervious cross-linked thermosetting resins. Other suitable polishing agents will be obvious to those skilled in the art.

The polishing material is generally present in the solid or pasty compositions in weight concentrations of about 10 percent to about 99 percent. Preferably, it is present in amounts ranging from about 20 percent to about 75 percent in toothpaste, and from about 70 percent to about 99 percent in tooth powder.

Soaps or detergents may also be employed in the present invention to lower the surface tension to achieve increased prophylactic action, assist in achieving thorough and complete dispersion of the antiplaque agent and render the instant compositions more cosmetically acceptable. Suitable soaps include, for example, the soaps of high molecular weight fatty acids such as sodium and potassium soaps of myristic, stearic or palmitic acids and fatty acids mixtures of palm oil and coconut oil. Typical synthetic detergents include alkyl sulfates and sulfonates having alkyl groups of from about 8 to about 18 carbon atoms, such as sodium lauryl sulfate, the sulfated fatty alcohols derived from coconut oil and palm oil, etc. The soaps typically comprise up to about 5 percent by weight of the dentifrice composition.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine, APM (aspartylphenylalanine, methyl ester), saccharine and the like. Suitably, flavor and sweetening agents may together comprise from about 0.1 percent to 5 percent of the preparation.

Toothpastes, creams and gels typically contain a natural or synthetic thickener or gelling agent in proportions of about 0.1 percent to about 10 percent, preferably about 0.5 to about 5 percent, by weight. Suitable gelling or thickening agents include for example, water-soluble salts of cellulose ethers such as sodium carboxymethyl cellulose and sodium carboxymethyl hydroxyethyl cellulose; natural gums such as gum karaya, gum arabic, and gum tragacanth; and colloidal magnesium aluminum silicate or finely divided silica.

Suitable humectants which may be employed in compositions of the invention include glycerine, propylene glycol, sorbitol, polypropylene glycol and/or polyethylene glycol and other polyhydric alcohols. The humectants may comprise 10 to 90 percent by weight of the dentifrice composition.

It has also been surprisingly found that in the presence of a cyclic alkylamine or cyclic amine of the present invention, the inclusion of a cationic antimicrobial compound in the dentifrice results in the antimicrobial compound being retained in the oral cavity for a longer period of time than in the absence of a cyclic alkylamine or cyclic amine. While not wishing to be bound by theory, it is believed that the cyclic alkylamines and cyclic amines of the present invention have an affinity for the tooth surface creating an anionic surface on the teeth to which cationic antimicrobial compounds are beneficially attracted. The antimicrobial is therefore retained within the oral cavity for a longer period of time due to the electrostatic forces between the anionic tooth surface and the cationic antimicrobial. The ability of an antimicrobial compound to be retained and remain active within the oral cavity to exert an antiplaque effort for a longer period of time is referred to as the "substantivity" of the compound. The terms "antimicrobial" and "antibacterial" as used herein refer to the ability of a cationic compound to inhibit the growth, reproduction or metabolism of microorganisms.

The enhanced substantivity of the antimicrobial compound aids in the prevention of dental calculus by inhibiting microorganisms responsible for the initial formation of dental plaque. The inhibition of microorganisms will also reduce the amount of volatile sulfur compounds produced by the putrefactive activity of the microorganisms, thus helping to control mouth malodor. It has also been surprisingly found that inclusion of an antimicrobial does not affect the calculus inhibiting ability of the cyclic alkylamines or cyclic amines used in the dentifrices of the present invention.

Antimicrobial compounds which are particularly useful in dentifrice compositions of the present invention are compounds which contain an organic amine where the nitrogen is capable of being positively charged in an aqueous environment, preferably organic amines which are capable of being protonated in an aqueous environment and quaternary ammonium compounds.

Among the most common antibacterial quaternary ammonium compounds used in oral compositions are cetylpyridinium chloride, benzethonium chloride, also known as Hyamine 1622 or di-isobutyl(phenoxy-ethoxyethyl dimethylbenzyl ammonium chloride) and sanguinarine. Antibacterial quaternary ammonium compounds useful in the present invention include those represented by the formula

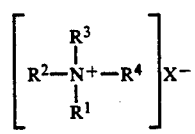
(V)

and formula

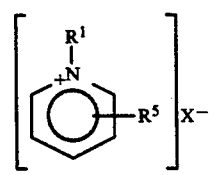
(VI)

wherein
$R^1$ is a $C_8$-$C_{20}$ alkyl;
$R^2$ is benzyl or $C_1$-$C_{12}$ alkyl;
$R^3$ and $R^4$ are independently a $C_1$-$C_7$ alkyl or —($CH_2$—CHOH—$CH_2$—O)$_n$H wherein n is 1 to 6;
$R^5$ is —H, a $C_1$-$C_7$ alkyl or —($CH_2$—CHOH—$CH_2$—O)$_n$H wherein n is an integer from 1 to 6; and
$X^-$ is chloride ($Cl^-$), bromide ($Br^-$), iodide ($I^-$) or fluoride ($F^-$).

The quaternary ammonium compounds useful in the present invention are commercially available or may be obtained by those of ordinary skill in the art without undue experimentation. For example, they may be produced by reacting alkyl halides with ammonia or primary amines, or by reacting a tertiary amine, pyridine or pyridine derivative with an alkyl halide. See, for example, Zoltewicz and Deady, *Adv. Hetrocycl. Chem.* 22, 71-121 (1978); U.S. Pat. Nos. 2,446,792; 2,295,504 and 4,994,199, the teachings of which are hereby incorporated by reference.

Other quaternary ammonium compounds which can be employed in dentifrices of the present invention include the following:

Pyridinium chlorides containing alkylthiomethyl or alkoxymethy hydrophobic groups as disclosed by Weglowski et al., *J. Phar. Sci.,* 80; 91-85 (1991), the disclosure of which is hereby incorporated by reference, the quaternary ammonium compounds having the formula

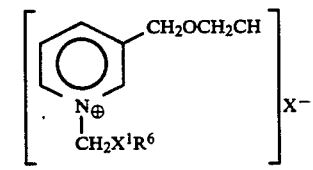

wherein X is as defined herein before and $X^1$ is oxygen or sulfur; and
$R^6$ is a $C_4$-$C_{16}$ alkyl or benzyl.

Quaternary ammonium compounds that are esters of betaine and fatty alcohols, as disclosed by Linstedt et al., *AntimicrobialAgentsand Chemotherapy,* 39; 1949-1954 (1990), the disclosure of which is hereby incorporated by reference, the quaternary ammonium compounds having the formula

$(CH_3)_3N^\oplus$—$CH_2C(O)OR^7$;

wherein $R^7$ is a $C_{10}-C_{18}$ alkyl; and physiologically acceptable salts thereof.

Sanguinarine and sanguinaria, sanguinaria being an extract from the bloodroot plant *Sanguinaria candensis*, the extract containing benzophenanthridine alkaloids such as sanguinarine, chelerythrine, protopine, homochelidonine and physiologically acceptable salts thereof as disclosed in U.S. Pat. Nos. 4,145,412 and 4,406,881, the disclosures of which are hereby incorporated by reference. Sanguinaria is available in dentifrices under the trademark Viadent TM brand sanguinaria; the major active ingredient sanguinarine chloride salt having the formula Dodecyltrimethylammonium bromide, benzyl dimethylstearylammonium chloride, cetylpyridinium chloride, N-tetradecyl-4-ethylpyridinium chloride, sanguinaria and 5-amino-1,3,bis(2-ethyl-hexyl)-5-methylhexahydropyrimidine are preferred quaternary ammonium antibacterial agents used in dentifrices of the present invention.

Examples of antibacterial organic amines which can be protonated in aqueous environments and are useful in dentifrices of the present invention include the following:

Morpholine compounds as disclosed in U.S. Pat. No. 4,894,221, the disclosure of which is hereby incorporate by reference, the morpholine compounds having the formula wherein $R^8$ is a $C_8-C_{16}$ alkyl at the 2 or 3 position of the morpholino ring;

$R^9$ is a $C_2-C_{10}$ alkyl substituted with a hydroxy group at other than the alpha-position;

the sum of $R^8$ and $R^9$ being greater than or equal to 10 and preferably 10-20; and physiologically acceptable salts thereof.

Antibacterial secondary amines and amides as disclosed in *J. Antibacterial and Antifungal Agents*, 17; 371 (1989), the disclosure of which is hereby incorporated by reference, wherein the antibacterial compounds have the following formula wherein $R^{10}$ is a $C_{10}-C_{18}$ alkyl;

wherein each $R^{11}$ is independently $C_8H_{17}$ or $C_{10}H_{21}$;

wherein $R^{13}$ is a $C_9-C_{17}$ alkyl; or wherein each $R^{13}$ is independently $C_7H_{15}$ or $C_9H_{19}$; and physiologically acceptable salts thereof.

Dialkyl amines and N,N'-dialkylpolymethylenediamines as disclosed in *J. Antibacerial and Antifungal Agents*, 17; 579 (1989), the disclosure of which is hereby incorporated by reference, having the formula $$R^{14}-NH-R^{14}$$

wherein each $R^{14}$ is independently $C_8H_{17}$ or $C_{12}H_{25}$; or formula $$R^{15}-NH(CH_2)_nNH-R^{15}$$

wherein
each $R^{15}$ is independently a $C_7-C_{10}$ alkyl;
n is an integer from 2-5; and pharmaceutically acceptable salts thereof.

N'-Alkyl-N-(2-aminoethyl)piperidine compounds as disclosed by Murata et al., *J. Pharm. Sci.*, 80, 26–28 (1991), the disclosure of which is hereby incorporated by reference, the compounds having the formula wherein $R^{16}$ is a $C_{10}-C_{18}$ alkyl; and pharmaceutically acceptable salts thereof.

The ammonium compound 4-(2-propylenepentyl)-1-piperidinoethanol having the structure wherein $X^-$ is as defined hereinbefore. This antimicrobial is described in *J. Periodontal Research*, 18, pp. 429–437 (1983), as the Octapinal TM brand 4-(2-propylenepentyl)-1-piperidinoethanol (Ferrosan AB, Sweden).

Alkyl-N-betaine in combination with an alkyl-N,N-dimethylamine oxide; the alkyl-N-betaine having the structure

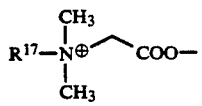

wherein $R^{17}$ is a $C_{10}-C_{18}$ alkyl; the alkyl-N,N-dimethylamine having the structure

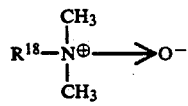

wherein $R^{18}$ is a $C_{10}-C_{18}$ alkyl; as disclosed in U.S. Pat. No. 4,839,158, the disclosure of which is hereby incorporated by reference.

Other antimicrobial agents which can be employed in the dentifrices of the present invention include biguanides such as chlorhexidine (1,6-bis-[$N^5$-(p-chlorophenyl)-N'biguanido]hexane; N'-(4-chlorobenzyl)-$N^5$-(2,4-dichlorobenzyl)biguanide; p-chlorophenyl biguanide; 4-chlorobenzylhydrylbiguanide; N-3-lauroxypropyl-$N^5$-p-chlorobenzylbiguanide; 5,6-dichloro-2-guanidinobenzimidazole; N'-p-chlorophenyl-$N^5$-laurylbiguanide; and their non-toxic acid addition salts. Chlorhexidine being the preferred biguanide antimicrobial agent used in the dentifrices of the present invention.

The antibacterial agents are typically employed in amounts such that the oral product contains between about 0.001 percent and 15 percent by weight of the agent. Preferably for desired levels of antiplaque effect, the finished oral product contains about 0.01 percent to about 5 percent and most preferably about 0.025 percent to 1.0 percent by weight of the agent.

The molar ratio of the quaternary ammonium compound in the oral composition to the cyclic amines of the present invention is preferably from about 5:1 to about 1:5, more preferably from about 3:1 to about 1:3, and most preferably about 1:1.

The cyclic amines of Formula III are the preferred amines of the present invention to be used in oral compositions in conjunction with cationic antimicrobial compounds. A preferred cyclic amine of Formula III is when n=2, m=4 and each R group is methylene phosphonic acid. The preferred cationic antimicrobial compound to be used in conjunction with the cyclic amine is cetylpyridinium chloride.

The dentifrices of the present invention may also be in a kit form, the kit comprising in a first compartment an orally acceptable vehicle containing one or more cyclic alkylamines or cyclic amines and in a second compartment an orally acceptable vehicle containing one or more cationic antimicrobial compounds. When the dentifrice is in a kit form, the compounds in the separate compartments may be applied to the oral cavity sequentially or mixed prior to application. When applied sequentially, it is preferred that the cyclic alkylamine or cyclic amine be applied to the oral cavity prior to the cationic antimicrobial compounds.

When mixing the cyclic alkylamine or cyclic amine with the cationic antimicrobial compound prior to application to the oral cavity, it may be necessary to increase their concentration to account for dilution effects which can occur upon mixing. Whether applying the cyclic alkylamine or cyclic amine and cationic antimicrobial compound sequentially or mixing prior to use, the concentration of the cyclic alklyamine, cyclic amine and cationic antimicrobial compound to which the oral cavity is exposed should be in the range given hereinbefore for their concentration in the final dentifrice product. For ease of use, it is desirable for the dentifrice to contain both the antimicrobial and cyclic alkylamine or cyclic amine in one composition.

A variety of other ingredients may be added to the separate compartment of a dentifrice kit, such polishing agents, soaps or detergents, flavoring and sweetening agents, and the like as described hereinbefore.

Surprisingly, it has also been found that inclusion of a metal ion in the oral composition with a cyclic amine and cationic antimicrobial compound does not interfere with the cationic antimicrobial compound being retained within the oral cavity for a longer period of time than when using an oral composition containing only a cationic antimicrobial compound. The molar ratio of the metal ion to cyclic amine is preferably from about 5:1 to 1:5, more preferably from about 3:1 to 1:3, and most preferably about 1:1.

In a preferred embodiment of the present invention, the cyclic amine is a cyclic amine of Formula III where n=2, m=4 and each R group is methylene phosphonic acid, the cationic antimicrobial compound is cetylpyridinium chloride and the metal ion is strontium ($Sr^{2+}$), magnesium ($Mg^{2+}$), tin ($Sn^{2+}$), zinc ($Zn^{2+}$), calcium ($Ca^{2+}$) or mixtures thereof. Preferably the metal ion is $Sn^+$ or $Ca^{2+}$, more preferably the metal ion is $Ca^{2+}$.

In the practice of this invention, an oral composition according to this invention, such as a mouthwash containing the cyclic amine or cyclic alkylamine and/or a cationic antimicrobial compound and/or a metal ion, may be prepared by unifying the components in conventional manner and applied to the teeth and gingiva.

The invention will be further clarified by a consideration of the following examples, which are intended to be purely exemplary of the present invention.

Abbreviations

CPC=cetylpyridium chloride
DOTMP=1,4,7,10-tetraazacyclododecane-1,4,7,10-tetramethylenephosphonic acid
PCTMP=3,6,9,15-tetraazabicyclo[9.3.1.]pentadeca-1(15),11,13-triene-3,6,9-trimethylenephosphonic acid
HAP=hydroxyapatite Preparation of Stock Solutions The water used in preparing the stock solutions and in the following examples was distilled, deionized water. 0.0045 M DOTMP. A stock solution of 0.0045 M 1,4,7,10-tetraazacyclododecane-1,4,7,10-tetramethylenephosphonic acid (DOTMP) was prepared by adding 0.6168±0.0001 g of solid DOTMP to a 60 mL beaker and bringing into solution with the addition of 20 mL of water by the dropwise addition of 1.0 N sodium solution which raised the pH of the solution to 7.4. This solution was transferred quantitatively to a 250 mL volumetric flask and diluted to the mark with water. 0.0015 M DOTMP. Twenty mL of a 0.0045 M DOTMP stock solution was loaded into a four ounce jar and then diluted with 40 mL of water to produce a 0.0015 M DOTMP solution. 0.0045 M CPC. A 0.0045 M solution of cetylpyridinium chloride (CPC) was prepared by adding 40 mL of water to a 60 mL beaker containing 0.4026±0.0001 g CPC (Aldrich Chemical Company, Inc.). This solution was transferred quantitatively to a 250 mL volumetric flask and diluted to mark with water. The final pH of this solution was 7. 0.0015 M CPC. A four ounce jar was loaded with 20 mL of 0.0045 M CPC stock solution and diluted with 40 mL of water to give a 0.0015 M CPC solution. 0.0015 M DOTMP/CPC. Twenty mL of a 0.0045 M DOTMP solution and 20 mL of a 0.0045 M CPC solution were loaded into a four ounce jar and then diluted with 20 mL of water to produce a 0.0015 M solution. 0.0015 M chlorhexidine. A 100 mL beaker was tared and loaded with 0.0455±0.0001 g of chlorhexidine (CH) (Aldrich; FW 505.46) and 60 mL water added to give a 0.0015 M chlorhexidine solution at pH =7.4. 0.0045 M PCTMP. A 0.0045 M solution of 3,6,9,15-tetraazabicyclo-[9,3,1]-tetradeca-1(15),11,13-triene-N,N',N''-trimethylene-phosphonic acid (PCTMP) was prepared by adding 0.0224±0.0001 g of PCTMP to a 10 mL volumetric flask and diluting to mark with water. The pH of this solution was adjusted to 7.0 with addition of a few drops of 1.0 N NaOH. 0.0015 M PCTMP/CPC. A 2.0 mL aliquot of a 0.0045 M stock solution of PCTMP was added to a four dram vial. To this vial was then added 2.0 mL of water and a 2.0 aliquot of 0.0045 M CPC stock solution. The final concentration of this formulation was 0.0015 M PCTMP and 0.0015 M CPC.

Preparation of Metal Chloride Solutions

Several 0.004275 molar metal chloride solutions were prepared by adding the listed number of grams of the metal chlorides given in Table I to 40 mL of water.

TABLE I

PREPARATION OF METAL CHLORIDE SOLUTIONS

| Solution | Solution with CPC | Metal | Formula | Wt. (g) added to 40 ml $H_2O$ | $FW^a$ |
|---|---|---|---|---|---|
| 1 | 2 | Calcium | $CaCl_2:H_2O$ | 0.0252 | 147.02 |
| 3 | 4 | Zinc | $ZnCl_2$ | 0.0234 | 136.28 |
| 5 | 6 | Iron* | $FeCl_3$ | 0.0278 | 162.22 |
| 7 | 8 | Strontium | $SrCl_2:6H_2O$ | 0.0456 | 266.62 |
| 9 | 10 | Tin | $Sn(IICl_2:2H_2O$ | 0.0386 | 225.63 |
| 11 | 12 | Magnesium | $MgCl_2:6H_2O$ | 0.0348 | 203.31 |
| 13 | 14 | Copper* | $CuCl_2$ | 0.0230 | 134.45 |

$^a$FW = formula weight
*These metals produced a cloudy solution when CPC was added.

To prepare each solution listed in Table I (numbers 1-14), 40 mL of a 0.004275 M metal chloride solution prepared as described above, was added to 40 mL of a 0.0045 M DOTMP stock solution. The pH of this solution was adjusted to 7.4 with a few drops of 1.0 N sodium hydroxide solution and the solution then divided into two 40 mL aliquots. To one solution, 20 mL of water was added to produce a 0.0015 molar concentration of DOTMP/0.0014 molar concentration of metal. To the other 40 mL aliquot, 20 mL of CPC stock solution (0.0045 M) was added to produce a 1:0.95:1 ratio of DOTMP:metal:CPC in solution with a 0.0015 molar concentration of DOTMP and CPC. Thus, solutions 1, 3, 5, 7, 9, 11 and 13 contained metal/DOTMP in solution and solutions 2, 4, 6, 8, 10, 12 and 14 contained metal/DOTMP/CPC in solution. The 0.004275 molar concentration of metal insured that a five percent excess of DOTMP ligand was present when these solutions were mixed.

Glycolysis pH Test

A sucrose solution was prepared by loading 1.0 g of sucrose (Imperial Pure Cane Sugar) into a 60 mL beaker and then adding 20 mL of water. To this solution was added 8.0 mL of pooled whole human saliva. The saliva was collected from donors who had been permitted to eat or drink anything prior to collection period, but had foregone any oral hygiene on the day of collection. Prior to the collection, each donor rinsed their mouth for thirty seconds with approximately 30 mL water, and after waiting 5 minutes, began collecting saliva for 30–40 minutes, keeping the collected saliva on ice.

To the saliva/sucrose solution was added 1.0 mL of brain/heart infusion broth containing *Streptococcus mutants* (American Type Culture Collections No. 25175, ATCC) and 1.0 mL of brain/heart infusion broth containing *Streptococcus sanguis* (ATCC #10556). These cultures had been inoculated into 40 mL of broth and grown at 37° C. for sixteen hours prior to adding to the saliva/sucrose solution. (Each broth contained approximately 60 million colony forming units at the time of addition.)

Aliquots of 0.75 mL of the above saliva/sucrose/bacterial solution was added to the test tubes containing various washed HAP suspension. These test tubes were capped and attached to a tube rotator and placed in a 37° C. incubator for sixteen hours. Following this incubation period, the rotator was removed from the oven and allowed to cool to ambient temperature. The pH of the solutions were checked with a pH meter using a pH electrode calibrated with pH 4, 7 and 10 buffers.

EXAMPLE 1

Prevention of bacterial adherence to HAP surfaces

Hydroxyapatite disks, (7.5–2.7 mm), obtained from Calcitek, Inc. were prepared by tying a short length of chromel wire around then and placing the other end of the wire into a rubber stopper to allow the disk to be suspended within a test tube. Separate disks where then treated by placing separate disks into 2 mL of the following test solutions for two minutes with occasional mixing: water (control); 0.0015 M chlorhexidine; 0.0015 M cetylpyridinium chloride; 0.001 M DOTMP; DOTMP/CPC 0.0015 M each; and 0.0015 M Corning DC-5700, a 42 percent by weight suspension 3-(trimethoxysilylpropyldimethyloctadecylammonium chloride in methanol. The disks were than each washed by placing them into 2 mL of water, and the washing repeated a second time.

Each of the six test samples were than placed into a test tube containing 8 mL of a growth medium of brain-heart infusion broth with 5 percent sucrose, the growth medium having been inoculated with 100 μL of *Streptococcus mutans*, ATCC #25125 (approximately $5.5 \times 10^7$ colony forming units). The tubes were then incubated at 37° C. Each day for a week, the sample disks were transferred to a new test tube containing fresh medium and S. Mutans. After one week, the samples were taken out, rinsed by dipping into water, and stained with Butler Red Coat, a dental plaque disclosing agent.

The amount of plaque on each disk was determined visually and rated according to the following scale:
0=no plaque
1=slight plaque
2=moderate coverage
3=complete coverage, light plaque
4=complete coverage, heavy plaque.

The plaque rating for each of the test samples was as follows:

water (control)=4;
chlorhexidine=3;
CPC=2;
DOTMP=1;
DOTMP/CPC=2.

The heaviest plaque growth was found on the control disk. Formulations containing an antimicrobial agent (chlorhexidine, CPC, and DOTMP/CPC all showed a reduction in plaque. The sample with DOTMP alone shows that the HAP surface has been modified so as to inhibit bacterial adherence without the use of an antimicrobial agent.

EXAMPLE 2

Absorbence of DOTMP onto a HAP surface

A 0.3 mM solution of DOTMP at pH 7 was prepared and injected on an HPLC (high performance liquid chromatography) system. The HPLC system was a Hamilton PR-X100 anion exchange column (4.1 mm×50 mm) with 0.016 M sulfuric acid at 1 mL/min as eluent, Dionex gradient pump, Dionex variable wavelength detector (set on 210 nm) and a VG PDP-11 data collection system. The DOTMP at this concentration exhibited a peak with a 6.25 minute retention time and an area of 9.16.

A 13.45 g portion of a hydroxyapatite suspension (24.5 percent by weight suspension of hydroxyapatite in phosphate buffer from Sigma Chemical Co.) was washed with 20 mL of water and then mixed with 20 mL of 0.3 mM DOTMP. After a contact time of about one minute, the hydroxyapatite was removed by filtration and the filtrate analyzed by HPLC for DOTMP. The analysis showed that less than 0.7 area units could be attributed to DOTMP, indicating that 93 percent of the DOTMP left the solution to adhere to the hydroxyapatite surface.

EXAMPLE 3

Absorbence of CaDOTMP onto a HAP surface

The calcium salt of DOTMP (1 mM Ca-DOTMP) was prepared by mixing DOTMP and calcium chloride in water and adjusting the pH up to 7,4 with 0.1N NaOH. A 1.1184 gram portion of hydroxyapatite suspension as described in Example 2 was washed with 12 mL of water and then resuspended in 10 mL of 1 mM Ca-DOTMP. After stirring overnight (about 16 hours) the suspension was filtered and the filtrate analyzed by HPLC as described in Example 2. This analysis showed that 98.5 percent of the DOTMP had come out of solution, presumable onto the hydroxyapatite surface.

The filtered hydroxyapatite with DOTMP attached to the surface was resuspended in 10 mL of water with stirring for 2 hours at room temperature. The suspension was then filtered and the filtrate analyzed by HPLC. This analysis showed no evidence for any DOTMP in solution indicating the DOTMP was not coming off of the hydroxyapatite surface with a large volume of water wash. The results also show that the addition of calcium ions does not interfere with the ability of DOTMP to attach to hydroxyapatite surfaces.

EXAMPLE 4

Reduction in adherence of salivary proteins to hydroxyapatite in the presence of DOTMP Hydroxyapatite disks (7.5×2.7 mm, Calciteck, Inc.) were separately placed in glass vials to which was then added either 2 mL of water (control) or 2 mL of 0.001 M DOTMP. The vials were capped and placed on an end-over-end rotator for 30 minutes. The supernatant was removed and the disks washed three times with 1 mL water used as a wash each time. Into each vial was then added 2 mL of salivary supernatant and the vials capped and placed on an end-over-end rotator for 19 hours. The salivary supernatant was obtained by centrifuging saliva, which had been collected from human volunteers who had refrained from oral hygiene after eating, at full speed on a IEC-HN-SII centrifuge (about 4,000 rpm). After the 19 hour period, the supernatant from each vial was gently removed and each disk washed gently for a brief time with 2 mL of water. The disks were then separately place in vials containing 1 mL of 0.1 N NaOH and sonicated for 2 minutes. A 200 µL aliquot of the supernatant from each vial was then mixed with 3.0 mL of water in a quartz cuvette and the absorbence measured at 600 nm (water reference) for each sample.

The control showed an average absorbence reading (7 readings) of 0.0167 absorbence units and the DOTMP exposed disk (6 readings) 0.00588 absorbence units. Thus, the DOTMP treated disks showed a 2.84 fold reduction in the amount of salivary material accumulated on the DOTMP treated disk versus a water treated disk.

EXAMPLE 5

Substantivity of DOTMP/CPC versus CPC using hydroxyapatite powders

As the surface portion of a tooth is composed of about 97 percent inorganic substances, about 1 percent organic substances and about 2 percent water, the inorganic substances being mainly hydroxyapatite, hydroxyapatite powder was used as a model for tooth enamel.

A 24.5 g portion of a hydroxyapatite suspension (purchased as a 24.5 percent by weight suspension of HAP in phosphate buffer from the Sigma Chemical Co., St. Louis, Mo.) was weighed out and washed with 3–30 mL portions of water to remove the phosphate buffer. The solid was resuspended in 60 mL of water to give an HAP suspension in water of about 100 mg HAP/mL of water. In each of two test tubes was placed 100 µL of this suspension which contained 10 mg of solid HAP. Into tube 1 was placed 4.5 mL or 0.0015 M cetylpyridinium chloride (CPC). Into tube 2 was placed 4.5 mL of a solution containing CPC at 0.0015 M and DOTMP at 0.0015 M, pH 7.75. Both tubes were capped and mixed by end-over-end rotation for 10 minutes. After this 10 minute period a 500 µL portion of each suspension was removed and filtered through a 0.22 micron syringe filter into a clean polystyrene test tube. A 200 µL aliquot of the filtrate was mixed with 3.0 mL of water in a quartz cuvette and the ultraviolet (UV) absorbence at 260 nanometers was measured. The tubes containing the suspension were then put back on the rotator for an additional 20 minutes at which time they were sampled as before. The tubes were then put back on the rotator for an additional 35 minutes and sampled again. The UV absorbence of the filtered solutions at these times points as well at time zero, which is the absorbence of the 0.0015 M solutions before exposure to the hydroxyapatite surface, are shown in Table II.

TABLE II

ADSORPTION OF CPC TO HYDROXYAPATITE OVER TIME

| Compound | UV Absorbance | | | | % Decrease |
|---|---|---|---|---|---|
| | 0 min. | 10 min. | 30 min. | 50 min. | |
| 1 CPC | 0.3892 | 0.3159 | 0.3108 | 0.3082 | 20.8 |
| 2 DOTMP/CPC | 0.3810 | 0.2610 | 0.2718 | 0.2562 | 32.8 |

These results show that the equimolar addition of DOTMP to CPC gives a 58 percent increase in the amount of CPC that is absorbed onto the hydroxyapatite.

To determine the retention of CPC on the HAP from repeated washing, the two treated HAP samples from above, which now contain CPC loaded in differing amounts, were isolated by centrifuging and discarding the supernatant. To each of the solids was added 3.1 mL of water which represents the final volume before centrifuging. The tubes were agitated by end-over-end rotation for 10 minutes after which 500 μL was removed and filtered through a 0.22 micron syringe filter. A 200 μL portion of this filtrate was added to 3.0 mL of water in quartz cuvette and the solutions absorbence at 260 nanometers was measured. The suspensions were then mixed end-over-end and samples taken as described above after an additional 20 and 45 minutes of mixing. The UV absorbence readings for this equilibrating wash of the two suspensions as a function of wash time is given in Table III. Also shown in Table III is the percentage of CPC calculated to be present on the hydroxyapatite that was found during these exposure times.

TABLE III

LOSS OF CPC FROM HYDROXYAPATITE INTO A WATER WASH

| Compound | Max. UV Ab-sorb* | 10 Min. Con-tact | % of Max. | 30 Min. Con-tact | % of Max. | 75 Min. Con-tact | % of Max. |
|---|---|---|---|---|---|---|---|
| CPC | 0.1310 | 0.0415 | 32 | 0.0435 | 33 | 0.0400 | 31 |
| DOTMP/ | 0.1700 | 0.0146 | 9 | 0.0183 | 11 | 0.0175 | 10 |

*This is the maximun UV absorbance expected if 100% of the CPC that was found attached to the hydroxyapatite came off and went into solution.

From this washing experiment, it is clear that the CPC is washed off of the hydroxyapatite by water to a much smaller degree (68 percent reduction) in the case of the DOTMP/CPC treated hydroxyapatite versus CPC treated alone. Letting the wash equilibrate for 30 and 75 minutes longer did not change these results.

EXAMPLE 6

Substantivity of DOTMP/CPC versus CPC using hydroxyapatite spheroids (SHAP)

Hydroxyapatite spheroids (SHAP) were purchased from BDH Chemicals Ltd, Poole, England. These were specially developed hydroxyapatite in the form of mechanically stable, porous spheroidal particles of unknown surface area.

Into each of two test tubes was placed 200 mg of SHAP. To tube 1 was added 2.0 mL of 0.0015 M CPC and to tube 2 was added 2.0 mL of 0.0015 M CPC which also contained 0.0015 M DOTMP. The two tubes were mixed by an end-over-end motion for 10 minutes and then centrifuged briefly to settle the fine particles which arose after agitation. A 200 μL aliquot from each tube was then removed and added to 3.0 mL of water in a quartz cuvette. The UV absorbence at 260 nanometers was then measured. The tubes were then placed back on the rotator and aliquots removed for measuring the UV absorbence after 4 and 24 hours of mixing. The initial UV absorbence of the 0.0015 M solutions and the solutions after exposure to SHAP as a function of time is shown in Table IV.

TABLE IV

ADSORPTION OF CPC ONTO SPHEROIDAL HYDROXYAPATITE

| Compound | UV Absorbence | | | | % of CPC Bound | uMoles* |
|---|---|---|---|---|---|---|
| | 0 min. | 10 min. | 4 hrs. | 24 hrs. | | |
| 1 CPC | 0.3747 | 0.3384 | 0.3316 | 0.3343 | 10.8 | 0.324 |
| 2 DOTMP/ CPC | 0.3832 | 0.2258 | 0.2377 | 0.2243 | 41.5 | 1.245 |

*Micromoles of CPC adsorbed onto 200 mg of Spheroidal Hydroxyapatite

These results indicate that the use of DOTMP at equimolar ratios to CPC causes a 3.84 fold increase in the amount of CPC that is adsorbed from solution by spheroidal hydroxyapatite as well as increased its affinity toward the hydroxyapatite surface relative to water washes.

To determine the retention of CPC on SHAP from repeated washing, each of the two hydroxyapatite solids from above were transferred to a disposable polypropylene column equipped with a frit (Bio-Rad Laboratories). The solution was allowed to gravity filter through the frit which holds back the solid spheroids. The last traces of solution were removed by blowing 10 mL of air through the tube which expels most of the solution. The remaining hydroxyapatite was then exposed to 2.0 mL of water for 10 minutes by an end-over-end rotation. After 10 minutes, a 200 μL aliquot of the supernatant was taken and added to 3.0 mL of water in a quartz cuvette. The UV absorption was then determined for these two solutions which corresponds to the first wash, 10 minutes exposure time. The spheroid containing solutions were then mixed for an additional 4 hours, at which time another 200 μL aliquot was taken for an UV measurement. A third 200 μL aliquot was taken for UV measurement after 24 hours of mixing. The spheroidal hydroxyapatite was then separated from the supernatant using the disposable column method described above and placed in 2.0 mL of water for the second wash. The second wash was sampled as previously described after mixing for 10 minutes and after mixing for 4 hours. A third wash was also performed, again using 2.0 mL of water and a 10 minute exposure time. The UV absorbence data from these samples is shown in Table V.

TABLE V

DESORPTION OF CPC FROM SPHEROIDAL HAP AS A FUNCTION OF
TIME AND DEGREE OF WATER WASHING

| Compound | Max. ABS if all CPS Solubilized* | 1st Wash, Exposure Time (ABS) | | | 2nd Wash, Exposure Time (ABS) | | 3rd Wash, 10 min. Exposure Time (ABS)/% of Max. |
|---|---|---|---|---|---|---|---|
| | | 10 min./% of Max. | 4 hrs./% of Max. | 20 hrs./% of Max. | 10 min./% of Max. | 4 hrs./% of Max. | |
| CPC | 0.0404 | 0.0372/ 92.1 | 0.0384/ 95.0 | 0.0390/ 96.5 | 0.0065/ 16.0 | 0.0036/ 8.9 | 0/0 |
| DOTMP/CPC | 0.1589 | 0.0222/ 14.0 | 0.0274/ 17.2 | 0.0367/ 23.1 | 0.0249/ 15.7 | 0.0341/ 21.5 | 0.0256/ 15.5 |

*This is the maximun UV absorbance if all the CPC on the hydroxyapatite was desorbed.

These results indicate that the use of DOTMP at equimolar ratios to CPC caused over a 10 fold increase in the amount of CPC retained on the spheroidal hydroxyapatite.

EXAMPLE 7

Improved antimicrobial substantivity

An 8 g sample of a HAP suspension (as described in Example 1) was weighed out and washed with 3–20 mL portions of water using a sintered glass filter funnel. The washed-solid HAP was then resuspended in 20 mL of water to give a milky white suspension containing about 100 mg solid HAP per mL of suspension.

Sample A

One mL of this HAP suspension was placed in each of 2 test tubes. Two mL of a 0.0015 M CPC solution was added to tube I and 2.0 mL of a solution composed of CPC (0.0015 M) and DOTMP (0.0015 M) at pH 7.44 was added to tube 2. The resulting suspensions were mixed thoroughly for 10 minutes on an end-over-end rotator, the tubes were then centrifuged for 3 minutes and the supernatant removed. The solid HAP in each tube was then resuspended in 3 mL of water by vigorous agitation with a plastic pipette, the suspensions centrifuged and the supernatants discarded. The solid HAP in each tube was resuspended in 2.0 mL of water and a 500 μL aliquot from each suspension was removed and placed into separate tubes labeled 1A and 2A. The remaining 1.5 mL of each suspension was recentrifuged and the supernatant discarded.

Sample B

The solid HAP remaining in each tube after removing Sample A, was resuspended in 3.0 mL of water, centrifuged, and the supernatant discarded. The HAP solid was resuspended in 3.0 mL of water a second time, centrifuged, and the supernatant discarded. The HAP from each tube was then resuspended in 1.5 mL of water and a 0.5 mL aliquot removed and labeled as 1B and 2B. The remaining 1.0 mL suspensions are centrifuged down and the supernatant discarded.

Sample C

The HAP remaining in each tube after the removal of Sample B was resuspended in 3.0 mL of water, centrifuged, and the supernatant discarded. The HAP solid was resuspended in 3.0 mL of water a second time, centrifuged, and the supernatant discarded. The resulting HAP in each tube was then resuspended in 1.0 mL of water and a 0.5 mL aliquot removed and labeled 1C and 2C. The remaining 0.5 mL of suspension was diluted with 3.0 mL of water, centrifuged, and the supernatant discarded.

Sample D

The HAP solid in each tube after the removal of Sample C was resuspended in 3.0 mL of water, centrifuged, and the supernatant discarded. The HAP was then resuspended in 0.5 mL of water and labeled as 1D and 2D.

The HAP samples labeled as "A" received 3 mL of water wash, those labeled as "B" received 11 mL of water wash, those labeled as "C" received 18.5 mL of water wash, and those labeled as "D" received 25.5 mL of water wash.

Into each of the 8 tubes, each containing about 0.5 mL of HAP (25 mg) suspension was added 0.5 mL of a 5 percent sucrose solution and 0.5 mL of saliva. The saliva was pooled 2 hours after breakfast from four human volunteers which had refrained from oral hygiene after eating. The tubes were shaken to mix the contents and the pH of each solution measured using a pH meter. The tubes are then capped and placed in an end-over-end rotator at about 50° C. overnight. The next day (t=13 hours) the tubes were allowed to cool and the pH of each suspension was measured. The results are shown in Table VI.

TABLE VI

| | pH DROP AS A FUNCTION OF HAP WASHINGS | | | | | | | | | | | |
|---|---|---|---|---|---|---|---|---|---|---|---|---|
| | Sample A (3 mL wash) | | | Sample B (11 mL wash) | | | Sample C (18.5 mL Wash) | | | Sample D (25.5 mL wash) | | |
| Compound | 0 hrs. | 13 hrs. | * | 0 hrs. | 13 hrs. | * | 0 hrs. | 13 hrs. | * | 0 hrs. | 13 hrs. | * |
| 1 CPC | 7.62 | 7.63 | −.01 | 7.60 | 6.31 | −1.29 | 7.69 | 6.20 | −1.49 | 7.75 | 6.41 | −1.34 |
| 2 DOTMP/CPC | 7.52 | 7.49 | 0.03 | 7.58 | 7.64 | 0.06 | 7.55 | 7.70 | 0.15 | 7.58 | 7.62 | 0.04 |

*pH change

A drop in pH means that there is little or no inhibition of bacteria such that the bacteria are able to metabolize the sucrose into organic acids, such as lactic acid, which then lowers the pH. The lack of a pH drop indicates that the bacteria are either dead or unable to metabolize sucrose which is a measure of how much CPC has been carried through the water washing on the hydroxyapatie solid.

These results show that the addition of DOTMP to a CPC solution causes more retention of CPC to hydroxyapatite which can then exert antimicrobial activity after longer amounts of washing. This test also shows enhanced substantivity of antimicrobial activity when using DOTMP together with CPC.

EXAMPLE 8

To further determine the substantivity of various combinations of cyclic amines/CPC/metal ions, the following washing procedure of the hydroxyapatite was done prior to performing a glycolysis pH test:

Twenty five mL of water were added to a 60 mL beaker containing 12.0 g of hydroxyapatite (HAP) in a buffer suspension (25 percent by weight solids from Sigma Chemical Co.). The HAP suspension was filtered through a medium glass fitted filter to obtain a HAP filter cake. The HAP filter cake was washed a second time with an additional 25 mL of water. The white solid filter cake containing 3.0 g of HAP without the buffer was resuspended with 30.0 mL of water to produce a 3.0 g/30.0 mL or 100 mg/mL suspension.

Two mL of the HAP suspension was transferred to each of several sterile-disposable polystyrene 5 mL test tubes labeled $D_1$-$D_n$ (where n=number of test solutions). Two mL of a test solution were then added to each test tube.

The tubes containing the HAP and test solution were capped and attached to a Tube Rotator and rotated end-over-end to allow the test solutions to contact the HAP for a total of ten minutes.

After mixing, the test tubes were placed in an Industrial Equipment Company (IEC) model K centrifuge and spun at setting 25 (mid-range) for ten minutes. The tubes were removed and the liquid layer decanted. A macropipettor was then used to add 3.0 mL of water to each test tube containing the centrifuged hydroxyapatite. The HAP solids were resuspended by vigorous in-and-out flowing action through the pipette. The tubes were again eentrifuged at setting 25 for ten minutes and the liquid layer decanted. Following the three milliliter wash step, the HAP solids were resuspended in 2.0 mL of water to produce the original 100 mg/mL suspension concentration. A 0.5 mL sample (containing 50 mg HAP) of this HAP suspension was removed and placed in each of several 5 mL polystyrene test tube labeled $A_1$-$A_n$. This sample A contains one fourth of the original HAP suspension which has been washed with three milliliters of water.

The remaining 1.5 mL in test tubes labeled $D_1$-$D_n$ were centrifuged for ten minutes, the test tubes removed, and the liquid layer decanted. Three milliliters of water were added to these test tubes and the HAP solids resuspended/washed using disposable pipettes. The tubes were centrifuged for ten minutes, the tubes removed and the liquid layer decanted. An additional three milliliters of water were added to these tubes and the HAP solids resuspended/washed by pipette. These tubes were again placed in the centrifuge and spun for ten minutes. The tubes were removed, the liquid layer decanted and 1.5 mL of water added to each tube. The HAP solids were resuspended to the original 100 mg/mL concentration and a 0.5 mL sample removed and placed in each of several 5 mL polystyrene test tube labeled $B_1$-$B_n$. This sample B contained 50 mg HAP solids which had been treated with test solution and then washed with a total of eleven milliliters of water.

The procedure given above was repeated a third and fourth time to create a series of test tubes labeled $C_1$-$C_n$ and $D_1$-$D_n$. The C samples contained HAP solids which had been treated with test solution and then washed with a total of 18.5 mL of water. The D samples contained HAP solids which had been treated with the test solution and then washed with a total of 25.5 mL water.

A glycolysis pH test was then performed as described above by adding 0.75 mL aliquots of the saliva/sucrose/bacterial mixture to the test tubes labeled $A_1$-$D_n$, each containing 0.5 mL of the treated washed HAP suspension.

Using the experimental procedure described above, the following compounds were tested for HAP substantivity: water (control); CPC; chlorhexidine (CH); DOTMP; and DOTMP/CPC. All compounds being tested present as 0.0015 M aqueous solutions. The results from this trial are shown in Table VII.

The solution of DOTMP/CPC shows markedly better antimicrobial activity after a series of washes than the other solutions tested.

TABLE VII

| pH AS A FUNCTION OF HAP WASHINGS | | | | | |
| --- | --- | --- | --- | --- | --- |
| Volume of Wash (mL) | Water | CPC[1] | CH[2] | DOTMP[3] | DOTMP/CPC[1,3] |
| 3 | 5.0 | 7.1 | 7.08 | 4.97 | 7.08 |
| 11 | 4.94 | 5.62 | 5.0 | 5.0 | 7.1 |
| 18.5 | 4.98 | 4.97 | 5.01 | 4.97 | 7.1 |
| 25.5 | 5.2 | 5.12 | 5.43 | 5.1 | 6.0 |

[1]CPC = cetylpyridinium chloride
[2]CH = chlorhexidine
[3]DOTMP = 1,4,7,10-tetraazacyclododecane-1,4,7,10-tetramethylenephosphonic acid

EXAMPLE 9

Using the experimental procedure described in Example 8, the following compounds were tested for HAP substantivity: water (control); cetylpyridinium chloride (CPC); DOTMP/CPC; and PCTMP/CPC. The compounds were tested as 0.0015 M aqueous solutions.

The results from this trial are shown in Table VIII. The HAP suspension treated with 0.0015 M CPC showed antimicrobial activity after being washed with 3 mL of water, however the level of CPC dropped considerably after being washed with 11 mL of water. The HAP suspension treated with a one-to-one solution of 0.0015 M DOTMP plus CPC formulation remained antimicrobial even after 25 mL of water washing. Likewise, the HAP suspension treated with a one-to-one PCTMP plus CPC formulation remained antimicrobial through 25 mL of water washing.

TABLE VIII

| pH AS A FUNCTION OF HAP WASHINGS | | | | |
| --- | --- | --- | --- | --- |
| Volume of Wash (mL) | Water | CPC* | DOTMP/CPC* | PCTMP/CPC* |
| 3 | 5.16 | 7.50 | 7.45 | 7.39 |
| 11 | 5.17 | 7.55 | 7.40 | 7.45 |
| 18.5 | 5.20 | 5.76 | 7.47 | 7.30 |
| 25.5 | 5.24 | 5.64 | 7.31 | 6.93 |

*CPC = cetylpryidinium chloride;
DOTMP = 1,4,7,10-tetraazacyclododecane-1,4,7,10-tetramethylenephosphonic acid;
PCTMP = 3,6,9,15-tetrabicyclo-[9.3.1]-tetradeca-1(15),11,13-triene-3,6,9-trimethylenephosphonic acid

EXAMPLE 10

Using the experimental procedure described in Example 8, the following compounds were tested for HAP substantivity: water (control); cetylpyridinium chloride (CPC); DOTMP/CPC; Calcium-DOTMP (Ca-DOTMP); and Ca-DOTMP/CPC. The compounds being tested present as 0.0015 M aqueous solutions and the Ca present as a 0.0014 M aqueous solution.

The results from this trial are shown in Table IX. The results show that DOTMP/CPC and Ca-DOTMP/CPC retained substantially more antimicrobial activity after a series of washes than the other solutions tested, indicating that the presence of calcium does not interfere with the CPC substantivity enhancing ability of DOTMP.

TABLE IX

| | pH AS A FUNCTION OF HAP WASHINGS | | | | |
|---|---|---|---|---|---|
| Volume of Wash (mL) | Water | CPC* | DOTMP/CPC* | Ca-DOTMP* | Ca-DOTMP/CPC* |
| 3 | 5.16 | 7.15 | 7.12 | 5.06 | 7.14 |
| 11 | 5.08 | 5.37 | 7.23 | 5.05 | 7.24 |
| 18.5 | 5.2 | 5.15 | 7.3 | 5.07 | 7.27 |
| 25.5 | 5.18 | 5.24 | 5.3 | 5.12 | 5.31 |

*CPC = cetylpyridinium chloride;
DOTMP = 1,4,7,10-tetraazacyclododecane-1,4,7,10-tetramethylenephosphonic acid;
Ca = calcium

EXAMPLE 11

Using the experimental procedure described in Example 8, the following compounds were tested for HAP substantivity: water (control); cetylpryidinium chloride (CPC); Sn-DOTMP; Sn-DOTMP/CPC; Zn-DOTMP; and Zn-DOTMP/CPC. The compounds being tested present as 0.0015 M aqueous solutions and the metals present as 0.0014 M aqueous solutions.

The results from this trial are shown in Table X. Both the Sn-DOTMP/CPC and Zn-DOTMP/CPC solutions displayed substantivity through a series of washes as measured by the retention of antimicrobial activity, with the Sn-DOTMP/CPC solution showing the greatest substantivity.

TABLE X

| | pH AS A FUNCTION OF HAP WASHINGS | | | | | |
|---|---|---|---|---|---|---|
| Volume of Wash (mL) | Water | CPC* | Sn-DOTMP* | Sn-DOTMP/CPC* | DOTMP* | Zn-DOTMP/CPC* |
| 3 | 5.0 | 7.05 | 5.03 | 7.07 | 5.02 | 7.05 |
| 11 | 5.0 | 6.39 | 5.0 | 7.1 | 5.05 | 7.1 |
| 18.5 | 5.1 | 5.1 | 5.01 | 6.36 | 5.03 | 7.19 |
| 25.5 | 5.2 | 5.2 | 5.13 | 7.12 | 5.24 | 5.48 |

*CPC = cetylpyridinium chloride;
DOTMP = 1,4,7,10-tetraazacyclododecane-1,4,7,10-tetramethylenephosphonic acid;
Sn = tin;
Zn = zinc

EXAMPLE 12

Using the experimental procedure described in Example 8, the following compounds were tested for HAP substantivity: water (control); cetylpyridinium chloride (CPC); Sr-DOTMP; Sr-DOTMP/CPC; and Mg-DOTMP/CPC. The compounds being tested present as 0.0015 M aqueous solutions and the metals present as 0.0014 M aqueous solutions.

The results from this trial are shown in Table XI. Both the Sr-DOTMP/CPC and Mg-DOTMP/CPC solutions showed substantivity through a series of washes as measured by the retention of antimicrobial activity.

TABLE XI

| | pH AS A FUNCTION OF HAP WASHINGS | | | | | |
|---|---|---|---|---|---|---|
| Volume wash (mL) | Water | CPC* | Sr-DOTMP* | Sr-DOTMP/CPC* | Mg-DOTMP* | Mg-DOTMP/CPC* |
| 3 | 4.88 | 7.0 | 4.85 | 6.96 | 4.9 | 6.98 |
| 11 | 4.92 | 5.46 | 4.9 | 7.0 | 4.91 | 6.99 |
| 18.5 | 4.95 | 4.96 | 4.89 | 7.0 | 4.91 | 7.04 |
| 25.5 | 5.19 | 5.03 | 4.93 | 5.36 | 4.98 | 5.65 |

*CPC = cetylpyridinium chloride;
DOTMP = 1,4,7,10-tetraazacyclododecane-1,4,7,10-tetramethylenephosphonic acid;
Sr = strontium; and
Mg = magnesium

EXAMPLE 13

Using the experimental procedure described in Example 8, the following compounds were tested for HAP substantivity: water (control); cetylpyridinium chloride (CPC); Ca-DOTMP/CPC; Sn-DOTMP/CPC; Zn-DOTMP/CPC; Sr-DOTMP/CPC; Mg-DOTMP/CPC; Fe-DOTMP; and Cu-DOTMP. The compounds being tested present as 0.0015 M aqueous solutions and the metals present as 0.0014 M aqueous solutions.

The results from this trial are shown in XII. Of the metal complexes tested with DOTMP and CPC, Sn has the best substantivity as measured by the retention of antimicrobial activity.

TABLE XII

| | pH AS A FUNCTION OF HAP WASHINGS* | | | | | | | | |
|---|---|---|---|---|---|---|---|---|---|
| Volume of Wash (mL) | Water | CPC | Ca-DOTMP/CPC | Sn-DOTMP/CPC | Zn-DOTMP/CPC | Sr-DOTMP/CPC | Mg-DOTMP/CPC | Fe-DOTMP | Cu-DOTMP |
| 3 | 5.01 | 6.97 | 6.95 | 7.01 | 6.98 | 6.95 | 6.95 | 4.96 | 5.1 |

TABLE XII-continued

| | | | pH AS A FUNCTION OF HAP WASHINGS* | | | | | | |
|---|---|---|---|---|---|---|---|---|---|
| Volume of Wash (mL) | Water | CPC | Ca-DOTMP/ CPC | Sn-DOTMP/ CPC | Zn-DOTMP/ CPC | Sr-DOTMP/ CPC | Mg-DOTMP/ CPC | Fe-DOTMP | Cu-DOTMP |
| 11 | 5.13 | 6.3 | 7.03 | 7.05 | 7.01 | 7.01 | 7.01 | 4.98 | 5.01 |
| 18.5 | 5.11 | 5.22 | 7.11 | 7.07 | 7.03 | 7.04 | 7.05 | 4.94 | 5.12 |
| 25.5 | 5.13 | 5.21 | 5.83 | 7.11 | 5.28 | 5.31 | 5.4 | 5.04 | 5.19 |

*CPC = cetylpyridinium chloride;
DOTMP = 1,4,7,10-tetraazacyclododecane-1,4,7,10-tetramethylenephosphonic acid;
Ca = calcium;
Sn = tin;
Zn = zinc;
Sr = strontium;
Mg = magnesium;
Fe = iron (II) and
Cu = copper (II)

EXAMPLE 14

An in-vivo study was conducted to determine the ability of the test formulations containing phytic acid to inhibit the experimental formation of gingivitis in Beagle dogs.

Purebred female Beagle dogs, 2-3 years old, with naturally occurring gingivitis were randomly divided into groups of four animals each. After 14 days of adaptation, the teeth of the dogs were scaled to remove supragingival calculus and polished. One week following the prophylaxes, during which time oral care was maintained by brushing, a baseline gingivitis index was obtained as measured by the procedure of Loe, *J. Periodontol* 8, 610 (1967) and Loe and Silness, *Acta Odont Scand* 21, 533 (1963). After the initial gingivitis index reading, the teeth of each group were sprayed twice daily, five days per week, with approximately 10 mL of one of the following mouth rinses:

(A) cetylpyridium chloride (CPC);
(B) tin/DOTMP/CPC (Sn-DOTMP/CPC);
(C) calcium/DOTMP (Ca-DOTMP);
(D) DOTMP/CPC The cetylpryidinium chloride and DOTMP were present at a concentration of approximately 1.5 millimolar (mM) and the metal ions, calcium and tin, at approximately 1.4 mM.

The CPC solution was prepared by dissolving 1.096 g CPC in 30 mL of water. The solution was transferred to a 2.0 liter volumetric flask and diluted to the mark with water. The pH of the final solution was approximately 5-9.

The Sn-DOTMP/CPC solution was prepared by initially making separate solutions of Sn-DOTMP (0,447 g stannous fluoride and 1.674 g DOTMP in one liter) and CPC (1,096 g in one liter). The DOTMP was suspended in 50 mL of water and brought into solution with the addition of 50 percent by weight sodium hydroxide to bring the pH to about 7 prior to adding to the stannous fluoride solution. The Sn-DOTMP and CPC solution were then combined to give approximately 1.4 mM Sn, 1.5 mM DOTMP and 1.5 mM CPC.

The Ca-DOTMP solution was prepared by dissolving 0.419 g calcium chloride dihyrate in 50 mL of water and transferring to a two liter volumetric flask. The DOTMP was prepared by suspending 1.674 g DOTMP in 50 mL of water and then adding 50 percent by weight sodium hydroxide to bring the DOTMP into solution. The DOTMP solution was then added to the two liter flask and diluted to the mark with water. The final pH was approximately 7.4.

The DOTMP/CPC solution contained 1.096 g CPC and 1.674 g DOTMP. The DOTMP was prepared separately as described above, added to a two liter volumetric flask containing CPC dissolved in 30 mL of water, and then diluting to the mark with water. The final pH was approximately 7.66.

After four weeks of treatment, the gingival index was again measured. The results given in Table XIII, showing the change in gingival index, show that the DOTMP/CPC composition was the most effective composition of those tested for inhibiting deterioration of the gingival health. The Ca-DOTMP and Sn-DOTMP/CPC compositions gave a lower increase in the gingival index when compared to the cetylpyridinium chloride alone.

TABLE XIII

| Formulation[1] | Change in Gingival Index over 4 weeks |
|---|---|
| CPC | 0.528 |
| Sn-DOTMP/CPC | 0.312 |
| Ca-DOTMP | 0.300 |
| DOTMP/CPC | 0.124 |

[1]CPC = cetylpyridinium chloride;
DOTMP = 1,4,7,10-tetraazadodecane-1,4,7,10-tetramethylenephosphonic acid;
Sn = tin;
Ca = calcium

EXAMPLE 15

Compatibility of Calcium with DOTMP and CPC

To determine the compatibility of metal ions with DOTMP and CPC in solution, 15 µL incremental amounts of a 0.01 M CaCl$_2$ solution were added to 100 µL of a sample containing DOTMP, CaCl$_2$ and CPC, each component at a concentration of 1.5 mM (pH 5.65). The solutions were mixed and observed for precipitation. The results shown in Table XIV indicate that at least five calcium ions are compatible with DOTMP/CPC mixtures at these concentrations with no visible precipitate.

TABLE IV

| Total Amount of CaCl$_2$ added (µL) | Molar Ratio of DOTMP:Ca:CPC* | Observation |
|---|---|---|
| 0 (initial solution) | 1:1:1 | clear, water white |
| 15 | 1:2:1 | clear, water white |
| 30 | 1:3:1 | clear, water white |
| 45 | 1:4:1 | clear, water white |
| 60 | 1:5:1 | clear, |

TABLE IV-continued

| Total Amount of CaCl₂ added (μL) | Molar Ratio of DOTMP:Ca:CPC* | Observation |
|---|---|---|
| | | water white |

*DOTMP = 1,4,7,10-tetraazacyclododecane-1,4,7,10-tetramethylenephosphonic acid;
Ca = Calcium;
CPC = cetylpyridinuum chloride Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. An oral hygiene dentifrice, mouthwash, toothpaste, dental gel, toothpowder, chewing gum, lozenge or other oral hygiene product consisting essentially of an orally acceptable vehicle containing therein from about 0.001 to about 15 percent by weight of one or more quaternary ammonium compounds and an effective amount of, as an antiplaque agent one or more of 1,4,7,10-tetraazacyclododecane-1,4,7,10-tetramethylene phosphonic acid, 3,6,9,15-tetraazabicyclo-)9.3.1)-pentadeca-1(15),11,13-triene-N,N',N''-trimethylene-phosphonic acid or physiologically acceptable salts thereof.

2. A method for inhibiting the formation of dental plaque comprising administering to mammalian teeth a plaque inhibiting amount of an oral hygiene dentifrice, mouthwash, toothpaste, dental gel, toothpowder, chewing gum, lozenge or other oral hygiene product containing therein from about 0.001 to about 15 percent by weight of one or more quaternary ammonium compounds and an effective amount as an antiplaque agent one or more of 1,4,7,10-tetraazacyclododecane-1,4,7,10-tetramethylene phosphonic acid, 3,6,9,15-tetraazabicyclo-(9.3.1)-pentadeca-1(15)11, 13-triene-N,N', N''-trimethylene phosphonic acid or physiologically acceptable salts thereof.

3. The oral composition of claim 1 wherein the antiplaque agent is present in a concentration from about 0.5 millimolar to about 20 millimolar.

4. The oral composition of claim 1 wherein the cationic antimicrobial compound is a quaternary ammonium compound represented by one or more of the following formula

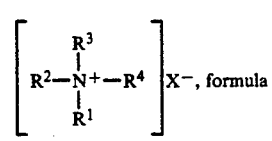

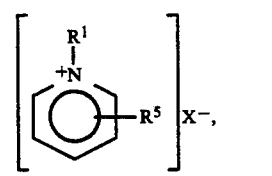

or a mixture thereof; wherein
$R^1$ is a $C_8$–$C_{20}$ alkyl;
$R^2$ is benzyl or $C_1$–$C_{12}$ alkyl;
$R^3$ and $R^4$ are independently a $C_1$–$C_7$ alkyl or —(CH₂—CHOH—CH₂—O)$_n$H wherein n is an integer from 1 to 6;
$R^5$ is —H, a $C_1$–$C_7$ alkyl or —(CH₂—CHOH—CH₂—O)$_n$H wherein n is an integer from 1 to 6; and
$X^-$ is chloride, bromide, iodide or fluoride.

5. The oral composition of claim 1 wherein the quaternary ammonium compound is cetylpyridinium chloride.

6. The method of claim 2 wherein the antiplaque agent is present in the oral composition in a concentration of from about 0.5 millimolar to about 20 millimolar.

7. The method of claim 2 wherein the cationic antimicrobial compound is one or more quaternary ammonium compounds represented by formula

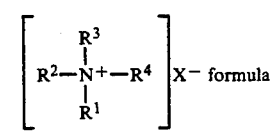

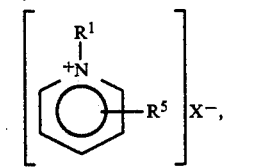

or a mixture thereof; wherein
$R^1$ is a $C_8$–$C_{20}$ alkyl;
$R^2$ is benzyl or $C_1$–$C_{12}$ alkyl;
$R^3$ and $R^4$ are independently a $C_1$–$C_7$ alkyl or —(CH₂—CHOH—CH₂—O)$_n$H wherein n is an integer from 1 to 6;
$R^5$ is —H, a $C_1$–$C_7$ alkyl or —(CH₂—CHOH—CH₂—O)$_n$H wherein n is an integer from 1 to 6; and
$X^-$ is chloride, bromide, iodide or fluoride.

8. The method of claim 7 wherein the antimicrobial quaternary ammonium compound is cetylpyridinium chloride.

* * * * *